United States Patent [19]

Marui et al.

[11] Patent Number: 5,258,286
[45] Date of Patent: Nov. 2, 1993

[54] METHOD OF TERMINATING ISOCITRATE DEHYDROGENASE REACTION

[75] Inventors: Yoji Marui; Takashi Nakano, both of Ousaka; Chozo Hayashi, Hyogo; Tuyosi Fujita, Ousaka; Isamu Takagaharay, Hyogo, all of Japan

[73] Assignee: Oriental Yeast Co., Ltd., Tokyo, Japan

[21] Appl. No.: 989,878

[22] Filed: Dec. 11, 1992

Related U.S. Application Data

[63] Continuation of Ser. No. 535,236, Jun. 5, 1990, abandoned, which is a continuation of Ser. No. 878,561, Jun. 24, 1986, abandoned.

[30] Foreign Application Priority Data

| Jul. 2, 1985 | [JP] | Japan | 60-143985 |
| Jul. 2, 1985 | [JP] | Japan | 60-143986 |

[51] Int. Cl.$^5$ .......................... C12Q 1/32; C12N 9/44; C12N 9/04
[52] U.S. Cl. ..................... 435/26; 435/184; 435/190; 435/12
[58] Field of Search ................. 435/190, 184, 26, 12, 435/26

[56] References Cited

U.S. PATENT DOCUMENTS

| 4,019,961 | 4/1977 | Klose et al. ............... 195/103.5 R |
| 4,742,001 | 5/1988 | Marui et al. ..................... 435/26 |

FOREIGN PATENT DOCUMENTS

| 0034213 | 8/1981 | European Pat. Off. . |
| 0149853 | 12/1984 | European Pat. Off. . |
| 0135092 | 3/1985 | European Pat. Off. . |
| 0199363 | 4/1986 | European Pat. Off. . |
| 1070603 | 6/1967 | United Kingdom . |
| 2026692 | 2/1980 | United Kingdom . |

OTHER PUBLICATIONS

Ingebretsen, O. C., et al. (1976) Arch. Biochem. Biophys. 176(2), 442–448.
O'Leary, M. H., et al. (1977) Biochemistry 16(6), 1129–1135.
Head, E. J. H., et al. (1980) Chem. Abst. 93:109474d.
Dedhia, D. et al. (1980) Chem. Abst. 92:71626u.
Chemical Abstracts (1984) 100:188,433d.
Wilson, V. J. C., et al. (1980) Chem. Abst. 92:176475x.
Gabriel, J. L., et al. (1985) Biochem. J. 229, 817–822.
Chemical Abstracts, vol. 103, No. 13, Sep. 30, 1985, p. 261, 103:100838t.
Chemical Abstracts, vol. 103, No. 3, Jul. 22, 1985, p. 263, No. 103:18977d.
Chemical Abstracts, vol. 92, No. 17, Apr. 28, 1980, p. 10, No. 92:140365x.
Wilkinson, J. H., *An Introduction to Diagnostic Enzymology*, Edward Arnold Ltd. pp. V–VIII, pp. 142–147 (1962).
*Biological Abstracts*, vol. 80, 1985, J. L. Gabriel et al.

*Primary Examiner*—Charles L. Patterson, Jr.
*Attorney, Agent, or Firm*—Browdy and Neimark

[57] ABSTRACT

Urea, creatinine, creatine, triglycerides, or the like in a specimen can be accurately determined by terminating an isocitrate dehydrogenase reaction by addition of a chelating agent in a system wherein NADP+ formed from NADPH is reproduced into NADPH in the conjoint presence of an isocitrate, metallic ions such as magnesium or manganese ions, and isocitrate dehydrogenase in assaying a substance by means of a reaction of NADPH to NADP+.

9 Claims, 1 Drawing Sheet

METHOD OF TERMINATING ISOCITRATE DEHYDROGENASE REACTION

This application is a continuation of application Ser. No. 07/535,236, filed Jun. 5, 1990, now abandoned, which application is a continuation of application Ser. No. 07/878,561, filed Jun. 24, 1986, now abandoned.

DETAILED DESCRIPTION OF THE INVENTION

The present invention is employed in assaying various substances in a specimen or in measuring activities of various enzymes. The present invention relates to a method terminating an isocitrate dehydrogenase reaction in a system of NADPH (nicotinamide adenine dinucleotidephosphate of reduced type)⇌NADP+ (nicotinamide adenine dinucleotidephosphate of oxidized type).

More specifically, the present invention relates to a method of terminating an isocitrate dehydrogenase (iCDH) reaction in a NADPH⇌NADP+ system to convert the system to a NADPH→NADP+ system.

Figure 1:
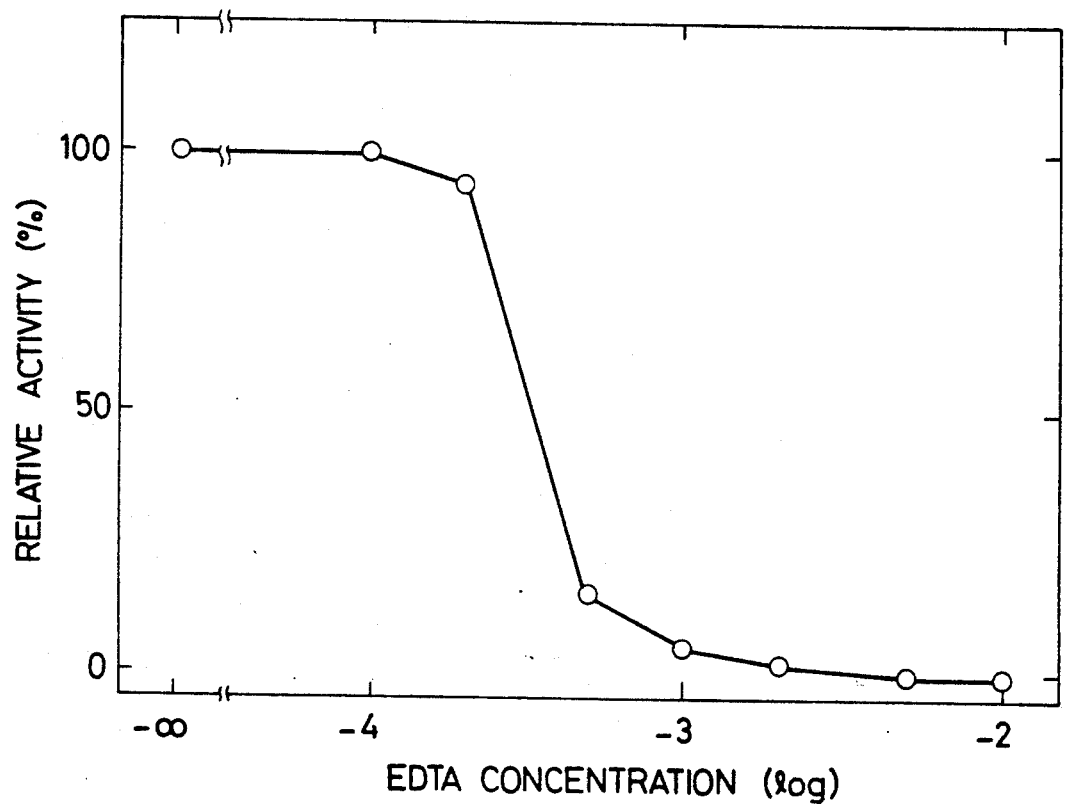
FIG. 1 is a diagram showing the influence of the molar EDTA concentration on the iCDH activity.

It is a common practice to detect urea, creatinine, creatine, guanine, adenosine, or the like generally present in a specimen such as urine or blood and to measure the activities of various enzymes concerned with substances as mentioned just above.

In the detection and enzymatic reactions of such substances, ammonia is formed, and the formed ammonia is converted into glutamic acid with the aid of GlDH (glutamate dehydrogenase). In this case, the amount of NADPH decreased in the coupled reaction of NADPH→NADP+ is determined by measuring absorption at 340 nm.

Since ammonia is yielded in this reaction system without fail, ammonia originally present in a specimen is involved in the measurement so that a difficulty is experienced in accurate determination.

This problem may be solved if only ammonia originally present in the specimen is preliminarily reacted with α-KG (α-ketoglutaric acid) with the aid of GlDH to convert the ammonia into glutamic acid. Since the system of ammonia→glutamic acid is accompanied by the conversion of NADPH→NADP+, NADPH must be reproduced according to the reverse reaction of NADP+→NADPH. In this case, a coupled reaction may be caused with isocitric acid as a substrate in the presence of iCDH (isocitrate dehydrogenase) and metallic ions such as magnesium or manganese ions. This reaction system can be expressed by the following formula (I).

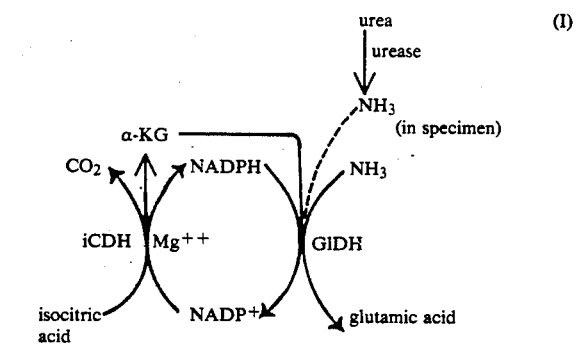

As shown in formula (I), consumption of ammonia in a specimen and assay of ammonia formed by decomposition of urea can be made according to the same coupled reaction. Accurate determination of ammonia formed by decomposition of urea can be performed first after consumption of ammonia in the specimen is completed and the reaction of NADP+→NADPH is completely terminated.

Therefore, the problem has been how to completely terminate the reaction of NADP+→NADPH in the system of NADPH⇌NADP+ in formula (I). It has not heretofore been known to completely terminate only the reaction of NADP+→NADPH.

It is a common practice to assay triglycerides in a specimen such as blood and to measure the activities of GOT (glutamic acid-oxaloacetic acid transaminase) and GPT (glutamic acid-pyruvic acid transaminase).

In the detection of triglycerides and various enzymatic reactions, pyruvic acid is formed at the final stage, and the formed pyruvic acid is converted into lactic acid with the aid of LDH (lactate dehydrogenase). The amount of NADPH decreased by the coupled reaction of NADPH→NADP+ in such conversion was determined by measuring absorption at 340 nm.

However, since pyruvic acid is yielded without fail in this reaction system, pyruvic acid and free glycerol originally present in a specimen are involved in the measurement. Thus, a difficulty has been experienced in performing accurate determination.

No problem may be involved if pyruvic acid originally present in the specimen is converted into lactic acid with the aid of LDH in a pretreatment. Since the system of pyruvic acid→lactic acid is accompanied by the conversion of NADPH→NADP+, NADPH must be reproduced according to the reverse reaction of NADP+→NADPH. In this case, a coupled reaction may be caused with isocitric acid as a substrate in the presence of iCDH and metallic ions such as magnesium or manganese ions. This reaction system can be expressed by the following formula (II).

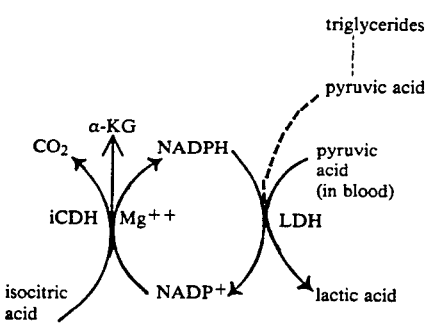

As shown in formula (II), consumption of pyruvic acid and free glycerol in a specimen and assay of pyruvic acid formed from triglycerides can be made according to the same coupled reaction. Accurate determination of pyruvic acid formed from triglycerides can be performed for the first time after consumption of pyruvic acid in the specimen is completed and the reaction of NADP+→NADPH is completely terminated.

Therefore, the problem has been how to terminate the reaction of NADP+→NADPH in the system of NADPH⇌NADP+ in formula (II). It has not heretofore been known to completely terminate only the reaction of NADP+→NADPH.

As a result of intensive investigations with a view to developing a method of completely terminating only a reaction of isocitric acid

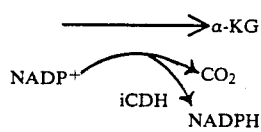

in the above-mentioned formulae (I) and (II), the inventors of the present invention have succeeded in completely terminating the reaction of isocitric acid

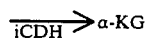

by addition of a metal-chelating agent.

The present invention provides a method of terminating an iCDH reaction in assaying a substance according to the reaction of NADPH to NADP+, characterized by terminating an iCDH reaction by adding a chelating agent in a system of reproduction of NADPH from NADP+ formed from NADPH in the conjoint presence of an isocitrate, metallic ions such as magnesium or manganese ions, and iCDH.

Metallic ions usable herein include those of magnesium, manganese, iron, copper, zinc, tin, and calcium. However, usable metallic ions are not limited to those ionic species mentioned above.

Usable chelating agents include EDTA and its salts, 1,2-bis(0-aminophenoxy)ethane-N,N,N',-N'-tetracetic acid and its salts, trans-1,2-cyclohexanediamine-N,N,N',N'-tetraacetic acid and its salts, dihydroxyethylglycine and its salts, 1,3-diaminopropanol-N,N,N',N'-tetraacetic acid and its salts, diethylenetriamine-pentaacetic acid and its salts, ethylenediaminedi-O-hydroxyphenylacetic acid and its salts, ethylenediaminediacetic acid and its salts, ethylenediaminedipropionic acid and its salts, hydroxyethylethylenediaminetriacetic acid and its salts, ethylenediaminetetrakis(methylenephosphonic acid) and its salts, glycol-etherdiaminetetraacetic acid and its salts, hydroxyethyliminodiacetic acid and its salts, iminodiacetic acid and its salts, diaminopropanetetraacetic acid and its salts, nitrilotriacetic acid and its salts, nitrilotripropionic acid and its salts, nitrilotris(methylenephosphonic acid) and its salts, and triethylenetetraminehexaacetic acid and its salts. However, usable chelating agents are not limited to those chelating agents mentioned above.

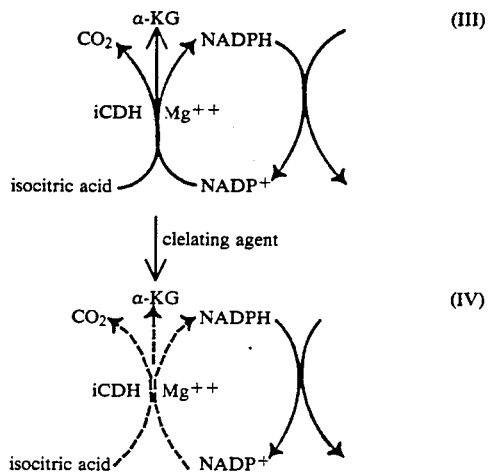

The dotted lines represent the reaction blocked by addition of the chelating agent.

According to the present invention, a conversion of formula (III)→formula (IV) as mentioned above is made by addition of a chelating agent and iCDH reaction is blocked. More specifically, complete consumption of ammonia or pyruvic acid in a specimen is effected according to formula (III), followed by addition of a chelating agent to the reaction system to terminate the reaction of NADP+→NADPH, while, thereafter, a substance to be assayed in the specimen is decomposed and NADPH is consumed by the reaction of NADPH-→NADP+ to perform accurate assay of the specimen.

The termination of the iCDH reaction by a chelating agent according to the present invention is very beneficial in that various assay reactions utilizing the reaction of NADPH→NADP+, can be carried out in a medium.

The amount of a chelating agent, for example, EDTA, to be added to the reaction system may be 10 mM or more. FIG. 1 is a diagram showing the influence of the EDTA concentration on the iCDH activity. It is understood that iCDH completely loses its activity at a concentration of 5 mM.

The method of terminating an iCDH reaction according to the present invention can be utilized in assaying a substance which yields ammonia upon decomposition thereof and in measuring the activity of an enzyme associated therewith. It can also be utilized in assaying a substance which produces pyruvic acid upon decomposition thereof and in measuring the activity of an enzyme associated therewith.

Specific examples of application of the present invention include the following methods of assaying respective urea, creatinine, creatine, and triglycerides.

(A) Method of Assaying Urea

GlDH, α-KG, NADPH, isocitric acid, metallic ions such as magnesium or manganese ions, and iCDH are admixed with a specimen to consume ammonia originally present in the specimen. Subsequently, a chelating agent is added to terminate the iCDH reaction, while, simultaneously or thereafter, urease is added to produce ammonia, which is determined to assay urea.

This reaction system can be expressed by the following formula (a).

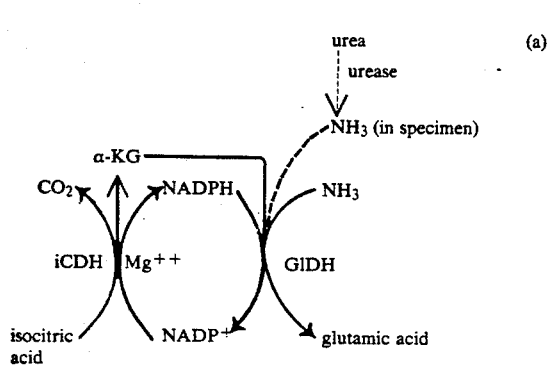

As shown in formula (a), consumption of ammonia in the specimen and assay of ammonia formed by decomposition can be made according to the same coupled reaction. Accurate assay of ammonia formed by decomposition of urea can be performed for the first time after consumption of ammonia in the specimen is completed and the reaction of $NADP^+ \rightarrow NADPH$ is completely terminated.

(B) Method of Assaying Creatinine

GlDH, α-KG, NADPH, isocitric acid, metallic ions such as magnesium or manganese ions, and iCDH are admixed with a specimen to consume ammonia originally present in the specimen. Subsequently, a chelating agent is added to terminate the iCDH reaction, while, simultaneously or thereafter, creatininase is added to produce ammonia, which is determined to assay creatinine.

This reaction system can be expressed by the following formula (b).

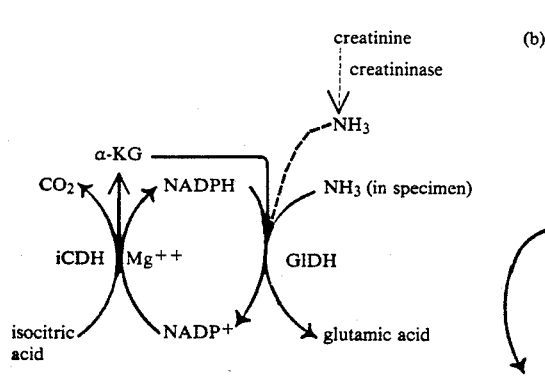

As shown in formula (b), consumption of ammonia in the specimen and assay of ammonia formed by decomposition can be made according to the same coupled reaction. Accurate assay of ammonia formed by decomposition of creatinine can be performed for the first time after consumption of ammonia in the specimen is completed and the reaction of $NADP^+ \rightarrow NADP$ is completely terminated.

(C) Method of Assaying Creatine

GlDH, α-KG, NADPH, isocitric acid, metallic ions such as magnesium or manganese ions, creatinine deiminase, and iCDH are admixed with a specimen to consume ammonia and creatinine originally present in the specimen. Subsequently, a chelating agent is added to terminate the iCDH reaction, while, simultaneously or thereafter, creatininase is added to produce ammonia, which is determined to assay creatine.

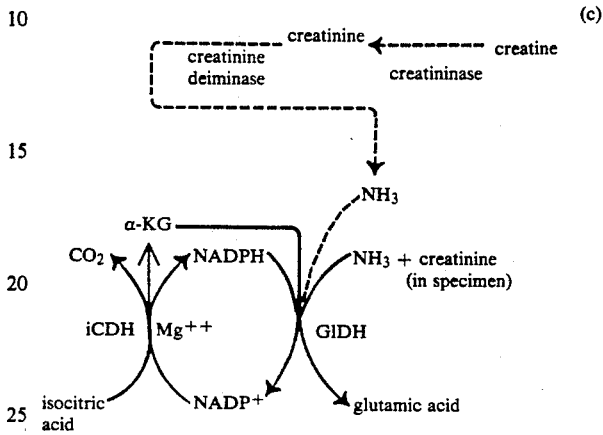

As shown in formula (c), assay of free creatine in the specimen can be made according to the same coupled reaction as in consumption of creatinine and ammonia in the specimen. Accurate assay of ammonia formed by decomposition of creatine can be performed for the first time after consumption of creatinine and ammonia in the specimen is completed and the reaction of $NADP^+ \rightarrow NADPH$ is completely terminated.

(D) Method of Assaying Triglycerides

LDH, NADH, ATP, PEP, glycerokinase, pyruvate kinase, isocitric acid, metallic ions such as magnesium or manganese ions, and iCDH are admixed with a specimen containing triglycerides to consume glycerol originally present in the specimen. Subsequently, a chelating agent is added to terminate the iCDH reaction, while, simultaneously or thereafter, lipase is added to produce pyruvic acid, which is determined to assay the triglycerides.

This reaction system can be expressed by the following formula (d).

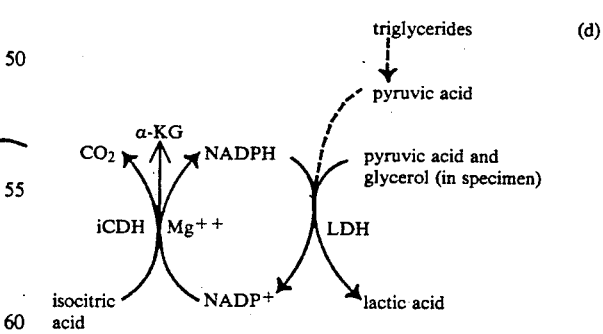

As shown in formula (d), consumption of free pyruvic acid and glycerol and assay of pyruvic acid formed from triglycerides can be made according to the same coupled reaction. Accurate assay of pyruvic acid formed from triglycerides can be performed for the first time after consumption of pyruvic acid and free glycerol originally present in the specimen is completed and the reaction of NADP+→NADPH is completely terminated.

Examples according to the present invention will now be described.

EXAMPLE 1

| | |
|---|---|
| MgCl$_2$ | 0.4 mM |
| isocitric acid | 1.6 mM |
| NADP+ | 1 mM |

A varied amount of EDTA was added to 3 ml of a 0.1M triethanolamine hydrochloride solution (pH 8.5) containing the above-listed ingredients to provide an EDTA concentration of 0 to 10 mM. Each of the resulting mixtures was kept at a temperature of 25° C., and admixed with 20 μl of iCDH of about 3 u/ml, followed by measurement of the iCDH activity based on an increase in absorption at 340 nm by spectrophotometry.

The results are shown in FIG. 1.

EXAMPLE 2

| | |
|---|---|
| α-KG | 5 mM |
| NADPH | 0.2 mM |
| isocitric acid | 5 mM |
| MgCl$_2$ | 0.2 mM |
| GlDH | 20 u/ml |
| iCDH | 2 u/ml |

30 μl each of specimens containing 160 mM of ammonia and urea (a varied concentration of 0 to 600 mg/dl in terms of nitrogen in urea form) was added to 2.4 ml of a 0.1M Tris hydrochloride solution (pH: 7.5) containing the above-listed ingredients. Each of the resulting mixtures was kept at a temperature of 37° C. for 5 minutes, and then admixed with 0.6 ml of a solution of a mixture of EDTA and urease to provide EDTA and urease concentrations of 5 mM and 0.1 u/ml, respectively, followed by determination of nitrogen in urea form in the specimen based on a decrease in absorption at 340 nm at 37° C. for 1 minute by spectrophotometry. The results are shown below.

| | Specimen No. | | | | | | |
|---|---|---|---|---|---|---|---|
| | 1 | 2 | 3 | 4 | 5 | 6 | 7 |
| Calcd. value of N in urea form (mg/dl) | 600 | 500 | 400 | 300 | 200 | 100 | 0 |
| Measured value (mg/dl) | 585 | 502 | 405 | 298 | 201 | 98 | 0 |

As shown above, the quantities of urea in the specimens could be measured, not being affected at all by ammonia of the high concentration contained in the specimens.

What is claimed is:

1. A method of terminating an isocitrate dehydrogenase reaction in a system wherein NADP+ formed from NADPH is reproduced into NADPH in the conjoint presence of an isocitrate, magnesium or manganese ions, and isocitrate dehydrogenase in assaying a substance which forms ammonia by enzymatic reaction by means of a reaction of NADPH to NADP+ coupled to an enzymatic reaction which consumes ammonia, which comprises terminating the isocitrate dehydrogenase reaction by adding a chelating agent to the reaction system.

2. In a method for assaying for an analyte in a sample which forms ammonia by enzymatic reaction by means of a reaction of NADPH to NADP+ coupled to an enzymatic reaction which consumes ammonia in the presence of an isocitrate, magnesium or manganese ions and isocitrate dehydrogenase, the improvement comprising terminating the reaction of isocitrate dehydrogenase by adding a chelating agent to the reaction system.

3. The method according to claim 2 wherein the analyte is selected from the group consisting of urea, creatinine, creatine, and triglycerides.

4. The method according to claim 2 wherein the chelating agent is selected from the group consisting of: EDTA and salts thereof; 1,2-bis-(o-aminophenoxy)ethane-N,N,N',N'-tetraacetic acid and salts thereof; dihydroxyethylglycine and salts thereof; 1,3-diaminopropanol-N,N,N',N'-tetraacetic acid and salts thereof; diethylenetriaminepentaacetic acid and salts thereof; ethylenediaminediacetic acid and salts thereof; ethylenediaminedipropionic acid and salts thereof; hydroxyethylethylenediaminetriacetic acid and salts thereof; ethylenediaminetetrakis(methylene-phosphonic acid) and salts thereof; glycoletherdiaminetetraacetic acid and salts thereof; hydroxyethyliminodiacetic acid and salts thereof; imiodiacetic acid and salts thereof; diaminopropanetetraacetic acid and salts thereof; nitrilotriacetic acid and salts thereof; nitrilotripropionic acid and salts thereof; nitrilotris(methylenephosphonic) acid and salts thereof; and triethylenetetraaminehexaacetic acid and salts thereof.

5. In a method of assaying a sample for an analyte which yields ammonia upon decomposition of said analyte, and ammonia originally present in the sample is first reacted with α-ketoglutaric acid to convert the ammonia in the sample to glutamic acid, the improvement comprising converting an isocitrate dehydrogenase reaction in a NADPH⇌NADP+ system to NADPH→NADP+ by adding a chelating agent to the reaction system to terminate the reaction of isocitrate dehydrogenase.

6. The method according to claim 5 wherein the analyte is selected from the group consisting of urea, creatinine, guanine, and adenosine and the sample is selected from the group consisting of urine and blood.

7. The method according to claim 5 wherein the isocitrate dehydrogenase reaction is coupled to an enzymatic reaction which consumes ammonia in the presence of an isocitrate, isocitrate dehydrogenase, and an ion selected from the group consisting of magnesium ion and manganese ion.

8. The method according to claim 5 wherein the chelating agent is selected from the group consisting of EDTA and salts thereof; 1,2-bis-(o-aminophenoxy)ethane-N,N,N',N'-tetraacetic acid and salts thereof; dihydroxyethylglycine and salts thereof; 1,3-diaminopropanol-N,N,N',N'-tetraacetic acid and salts thereof; diethylenetriaminepentaacetic acid and salts thereof; ethylenediaminediacetic acid and salts thereof; ethylenediaminedipropionic acid and salts thereof; hydroxyethylethylenediaminetriacetic acid and salts thereof; ethylenediaminetetrakis(methylene-phosphonic acid) and salts thereof; glycoletherdiaminetetraacetic acid and salts thereof; hydroxyethyliminodiacetic acid and salts thereof; iminodiacetic acid and salts thereof; diaminopropanetetraacetic acid and salts thereof; nitriliotriacetic acid and salts thereof; nitrilotripropionic acid and salts thereof; nitrilotris(methylenephosphonic) acid and salts thereof, and triethylenetetraaminohexaacetic acid and salts thereof.

9. The method according to claim 5 wherein the reaction takes place in the substantial absence of lactate dehydrogenase.

* * * * *